US012778431B2

(12) United States Patent
Mori et al.

(10) Patent No.: US 12,778,431 B2
(45) Date of Patent: Nov. 3, 2026

(54) LIVING BODY INFORMATION MEASURING INSTRUMENT AND METHOD FOR CONTROLLING LIVING BODY INFORMATION MEASURING INSTRUMENT

(71) Applicant: OMRON HEALTHCARE Co., Ltd., Kyoto (JP)

(72) Inventors: Kentaro Mori, Kyoto (JP); Takeshi Kubo, Kyoto (JP); Yasuo Asano, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 271 days.

(21) Appl. No.: 18/487,729

(22) Filed: Oct. 16, 2023

(65) Prior Publication Data

US 2024/0032803 A1 Feb. 1, 2024

Related U.S. Application Data

(63) Continuation of application No. PCT/JP2021/020511, filed on May 28, 2021.

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02141* (2013.01); *A61B 5/02225* (2013.01);
(Continued)

(58) Field of Classification Search
None
See application file for complete search history.

(56) References Cited

U.S. PATENT DOCUMENTS

2013/0261474 A1 10/2013 Kim, I
2016/0235307 A1 8/2016 Chou

FOREIGN PATENT DOCUMENTS

CN 112512415 A 3/2021
JP 2005-168600 A 6/2005
(Continued)

OTHER PUBLICATIONS

International Search Report (ISR) For International Application No. PCT/JP2021/020511, Dated Jul. 6, 2021.
(Continued)

*Primary Examiner* — Ankit D Tejani
(74) *Attorney, Agent, or Firm* — Colson Law Group, PLLC

(57) ABSTRACT

A biological information measurement device includes a blood pressure measurement unit including a blood pressure measurement control unit configured to control a cuff configured to compress a target measurement site of a subject, a pump configured to supply gas into the cuff, an exhaust valve configured to adjust exhaust of the gas from the cuff, and a pressure detection unit configured to detect a cuff pressure that is a pressure in the cuff, the blood pressure measurement unit being configured to measure a blood pressure of the subject, and an electrocardiographic measurement unit including an electrode provided on a target measurement site side of the cuff and configured to measure an electrocardiographic waveform by processing an electrical signal obtained through a plurality of electrodes that can come into contact with a skin of the subject.

16 Claims, 13 Drawing Sheets

(51) Int. Cl.

| | |
|---|---|
| ***A61B 5/021*** | (2006.01) |
| ***A61B 5/022*** | (2006.01) |
| ***A61B 5/318*** | (2021.01) |
| ***G16H 40/63*** | (2018.01) |

(52) U.S. Cl.
CPC ............ *A61B 5/318* (2021.01); *A61B 5/7203* (2013.01); *A61B 5/7235* (2013.01); *A61B 5/742* (2013.01); *G16H 40/63* (2018.01); *A61B 2560/02* (2013.01)

(56) References Cited

FOREIGN PATENT DOCUMENTS

| | | | | | |
|---|---|---|---|---|---|
| JP | 2007-195693 | A | | 8/2007 | |
| JP | 2014-36843 | A | | 2/2014 | |
| JP | 3214887 | U | | 2/2018 | |
| JP | 2018153487 | A | | 10/2018 | |
| JP | 2020-028421 | A | | 2/2020 | |
| WO | WO-2020039830 | A1 | * | 2/2020 | ............ A61B 5/742 |

OTHER PUBLICATIONS

International Preliminary Report (IPRP) For International Application No. PCT/JP2021/020511, Dated Feb. 28, 2022.
Examination Report issued on Nov. 14, 2025 in corresponding IN patent application No. 202317067210.
Office Action issued on May 7, 2026 in corresponding CN patent application No. 202180097086.2.

* cited by examiner

[FIG. 1]
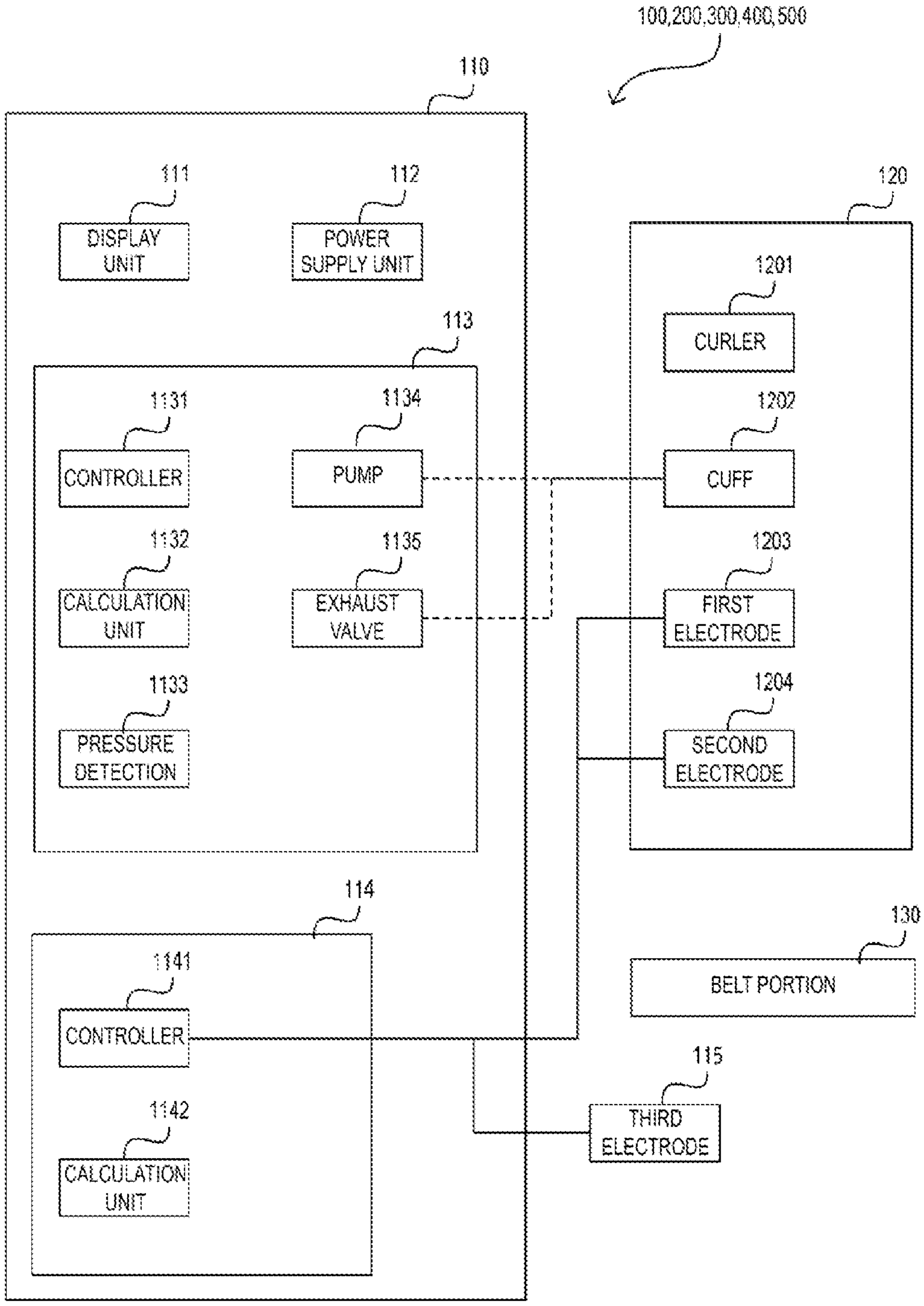

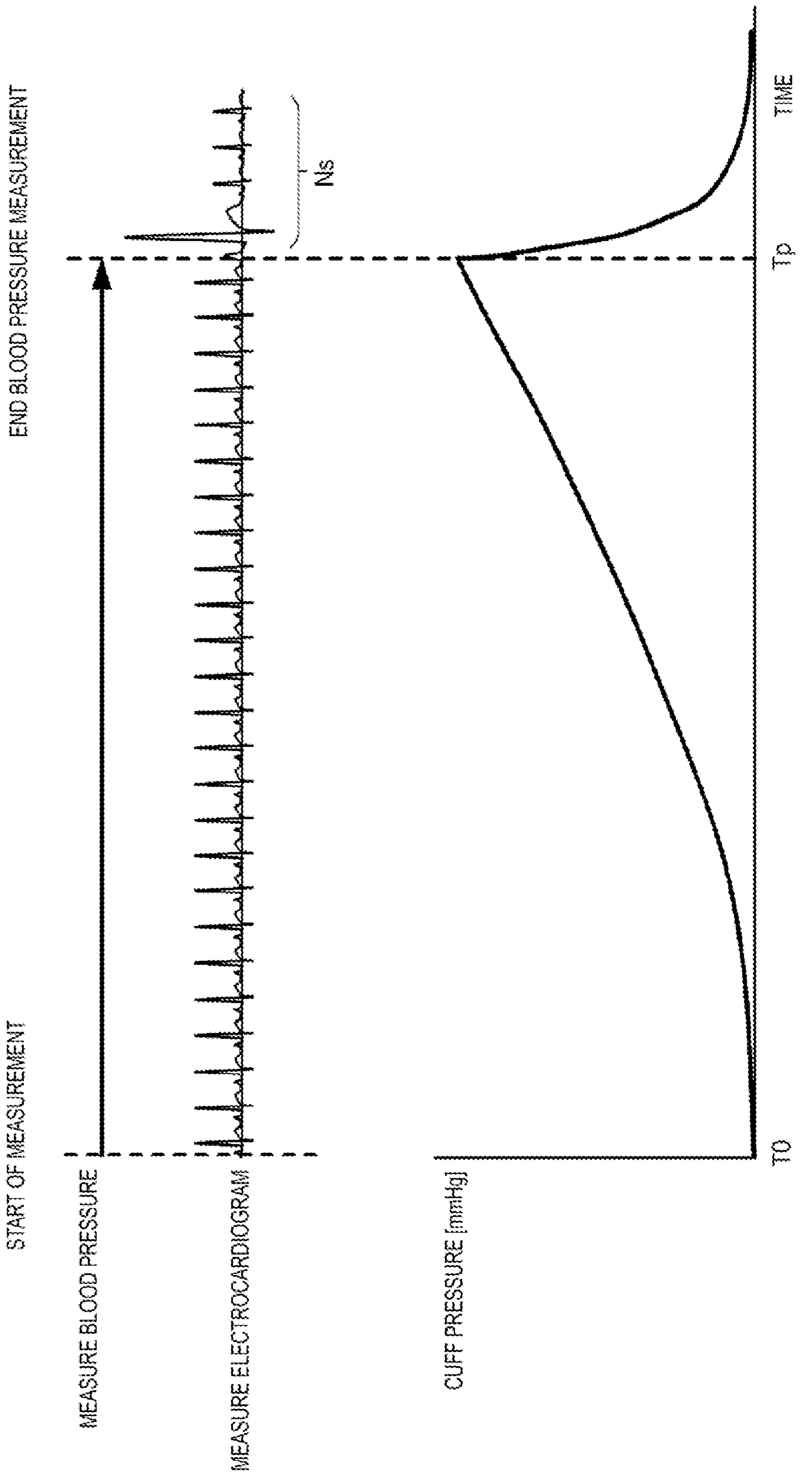
[FIG. 2]

[FIG. 3]
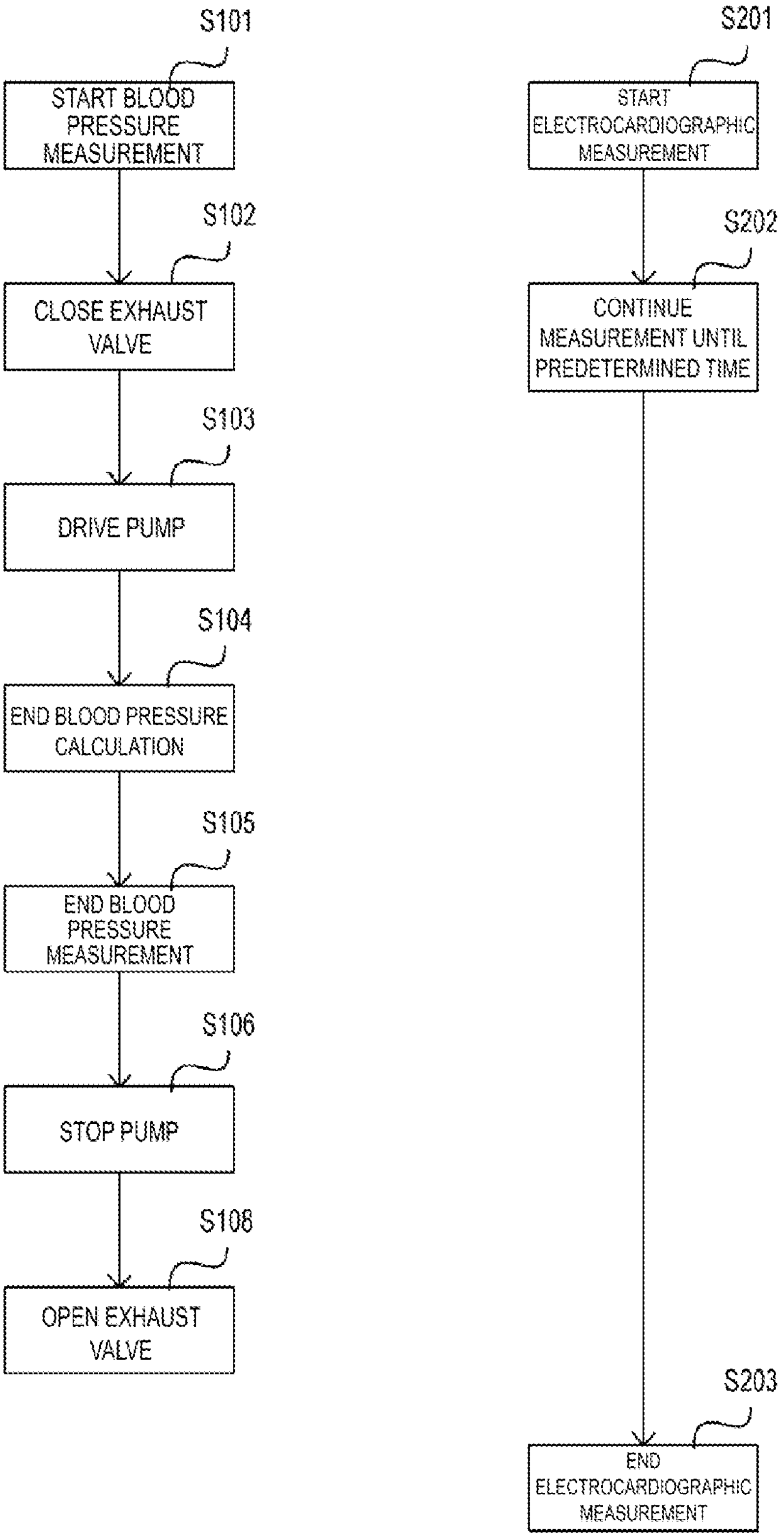

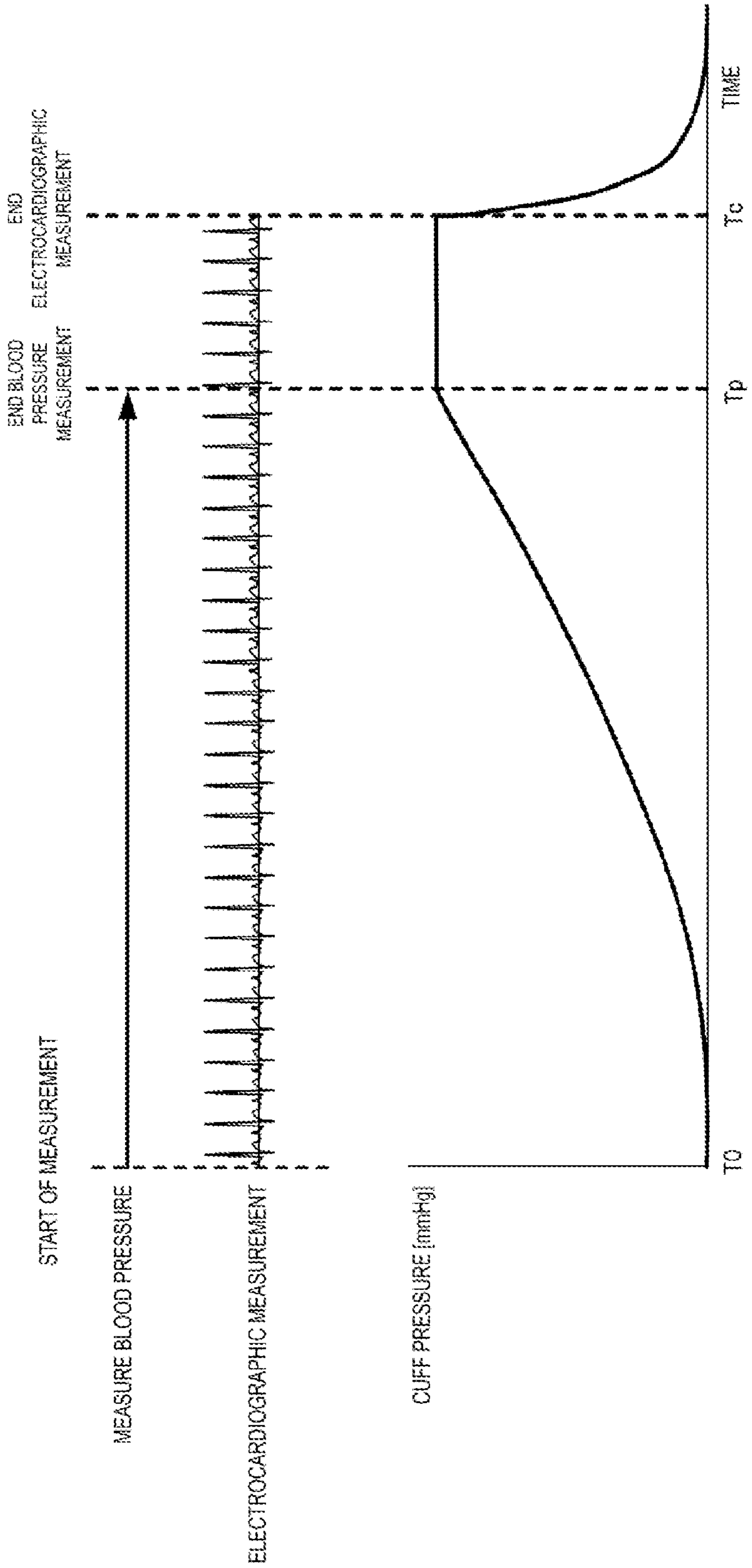
[FIG. 4]

[FIG. 5]
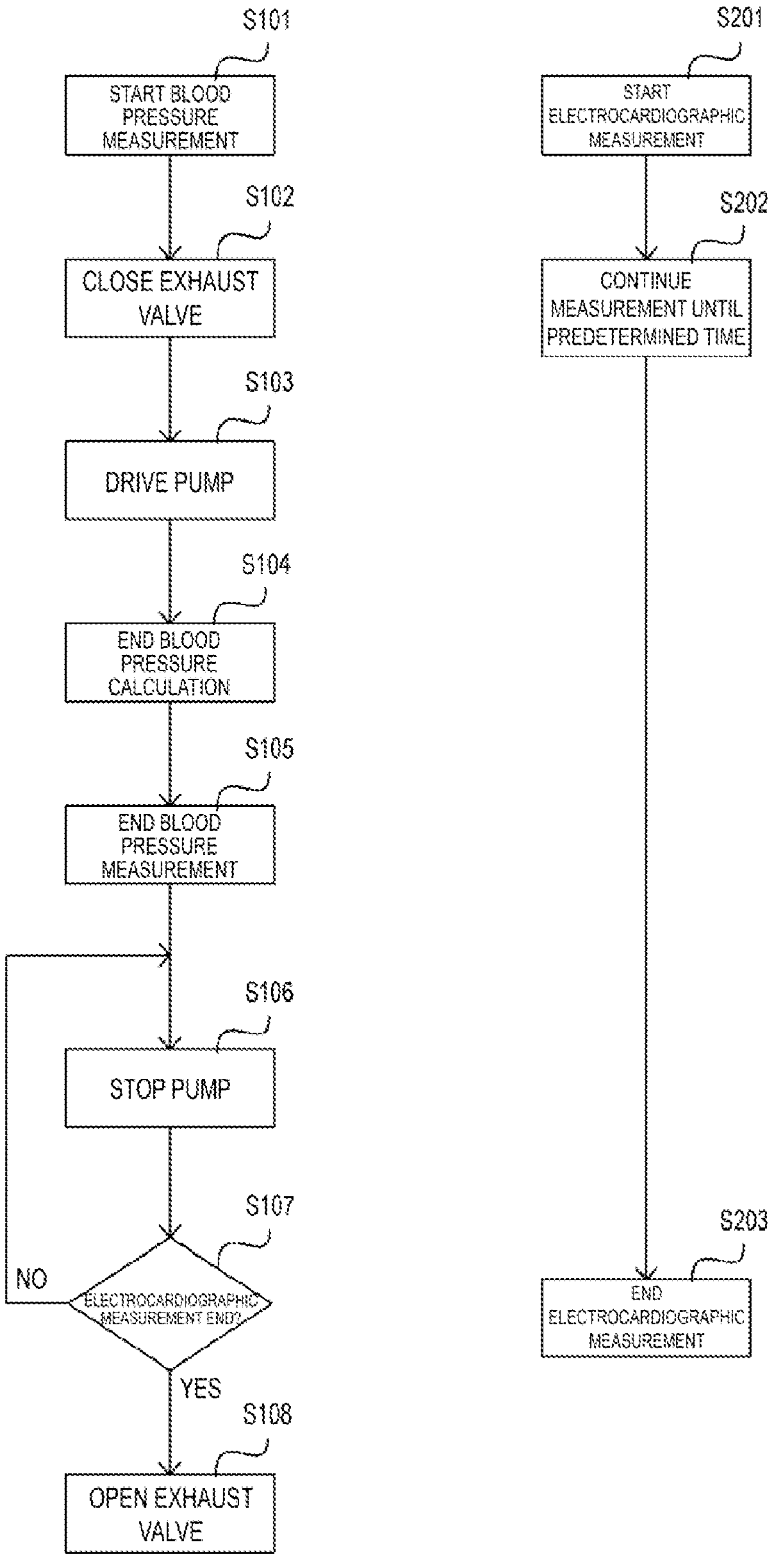

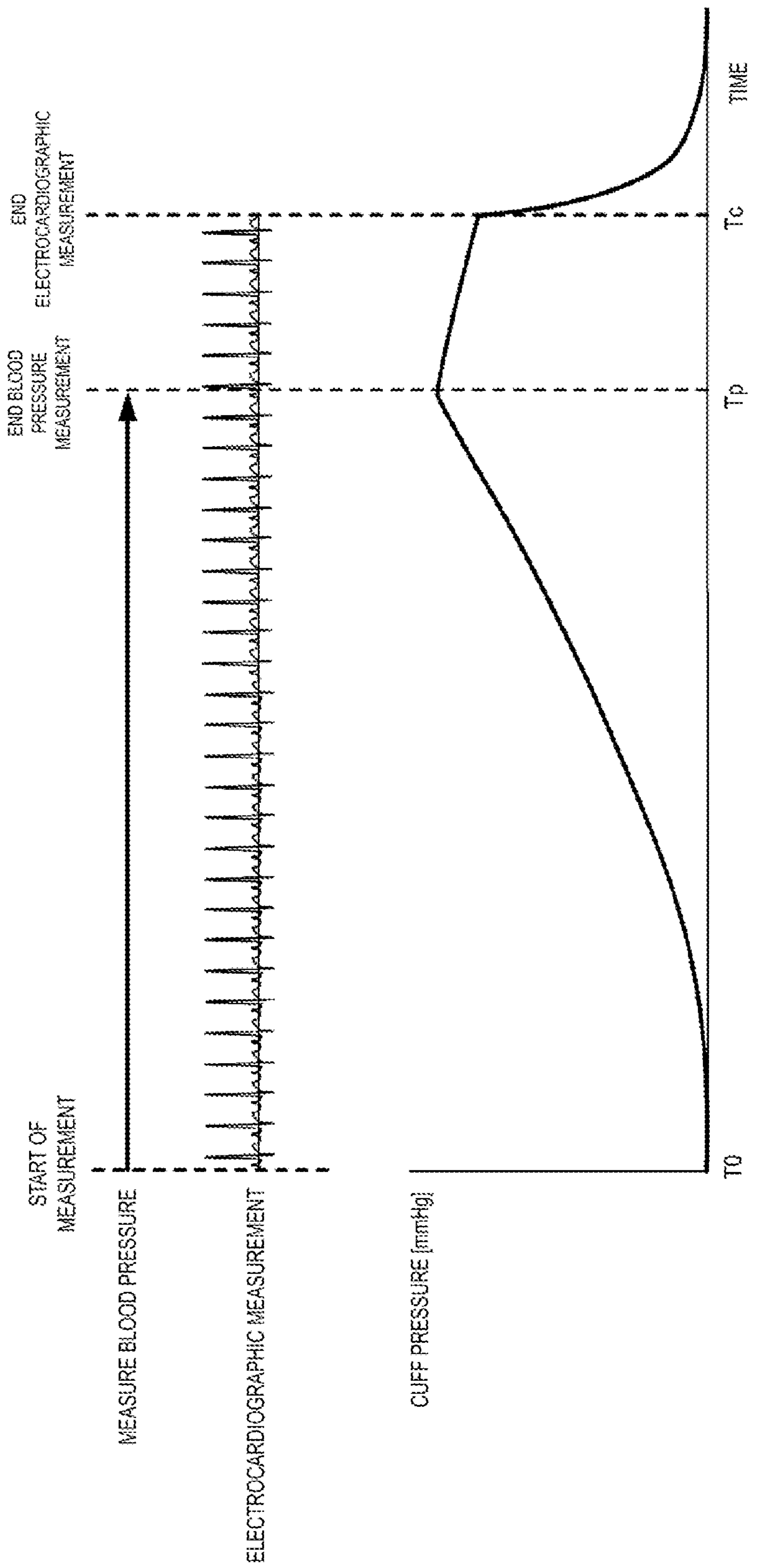
[FIG. 6]

[FIG. 7]
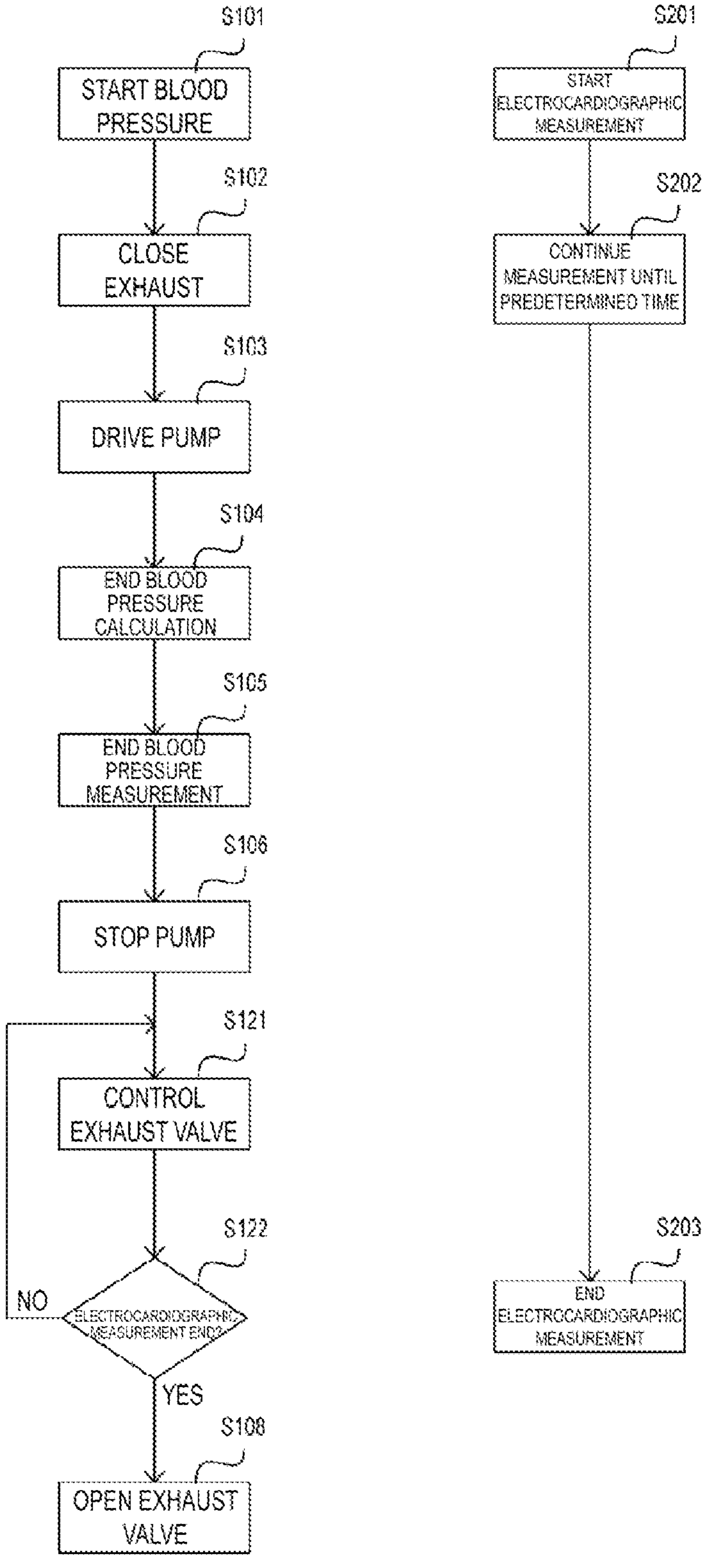

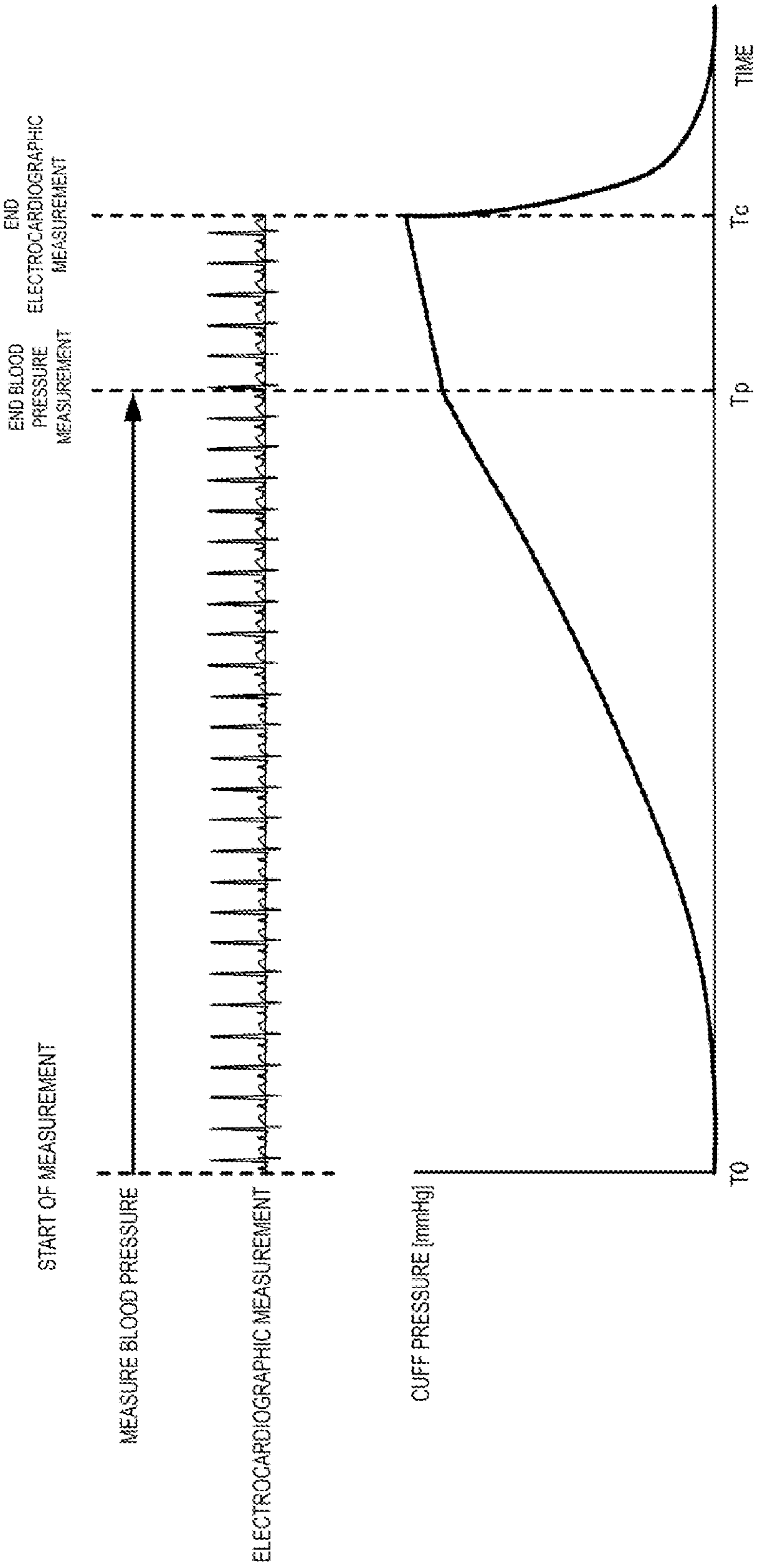
[FIG. 8]

[FIG. 9]
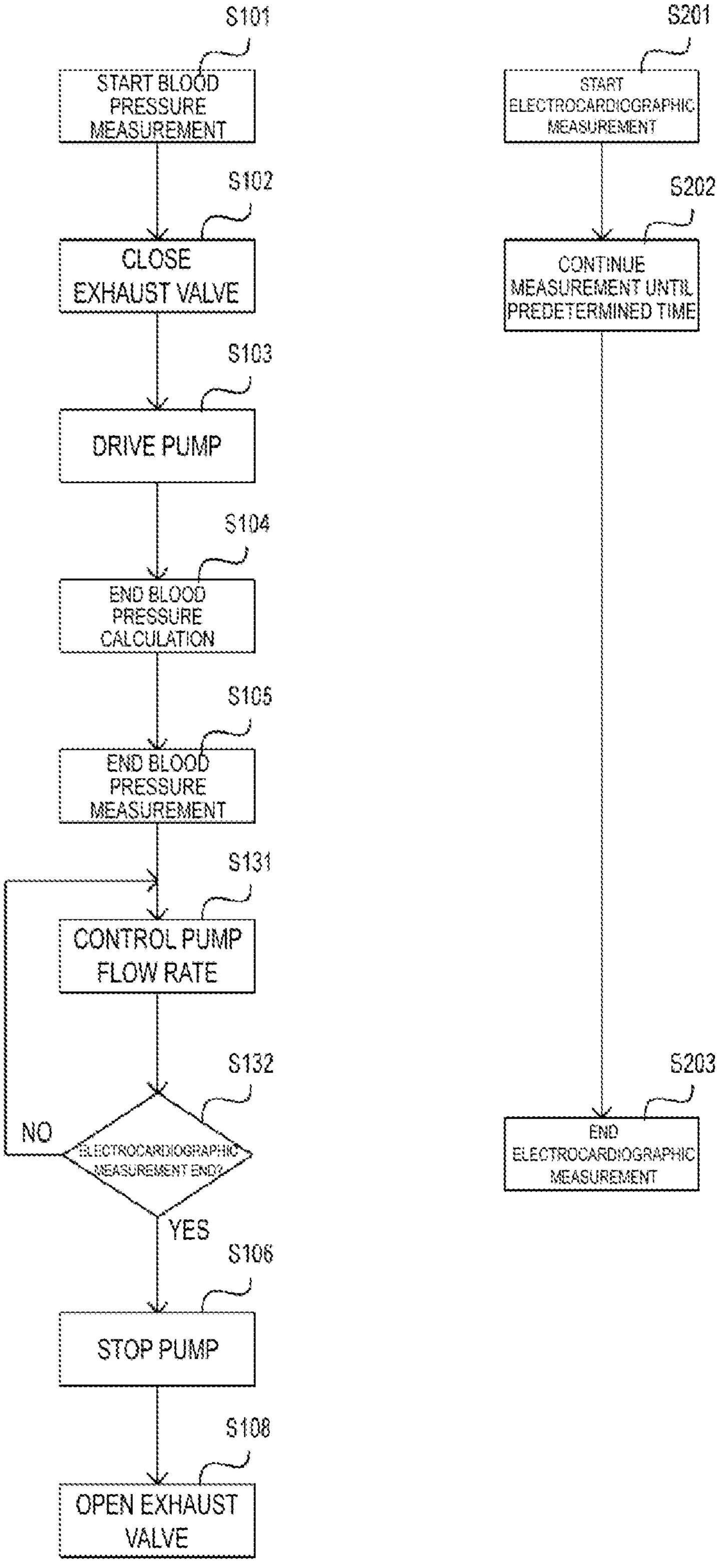

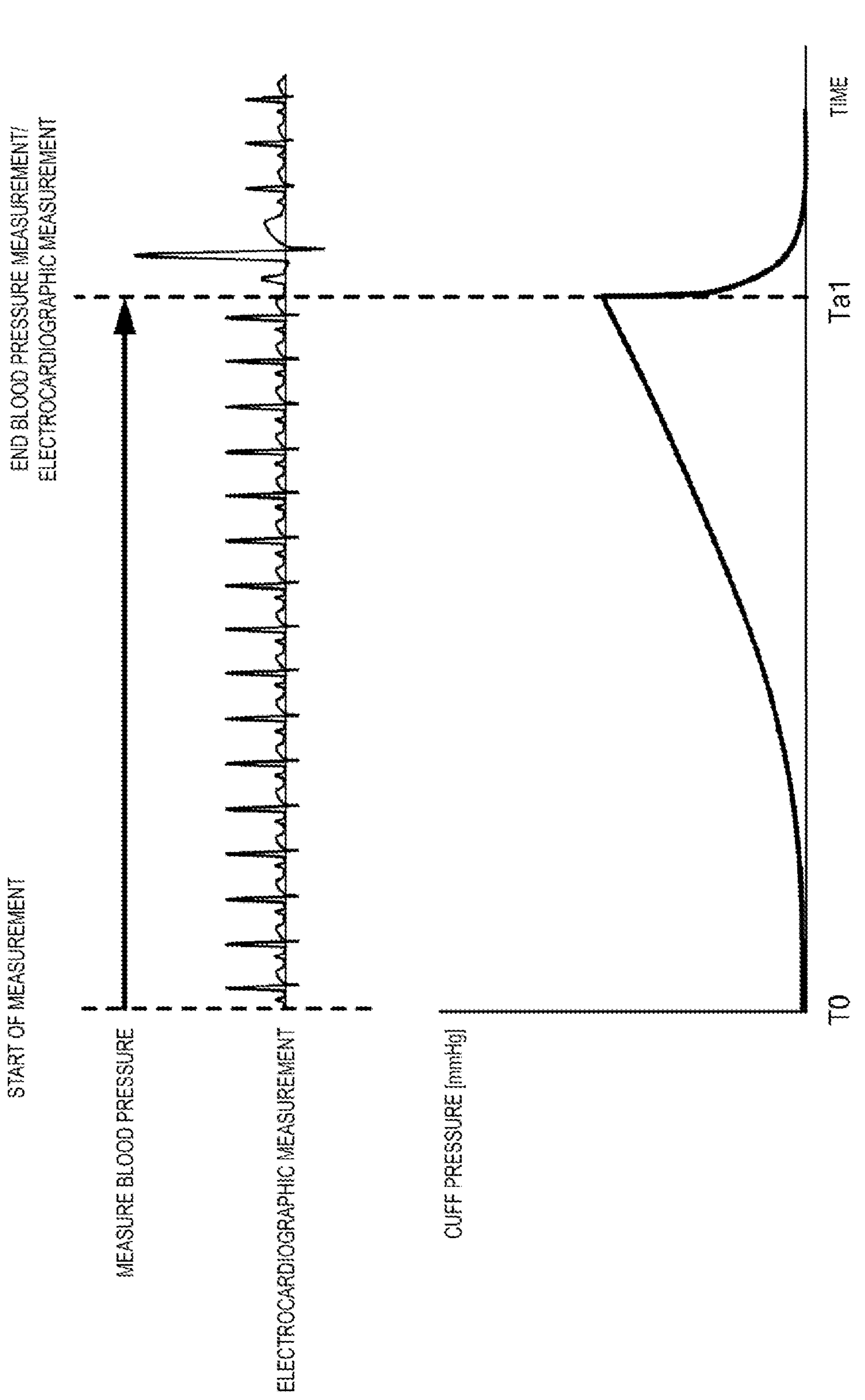
[FIG. 10]

[FIG. 11]
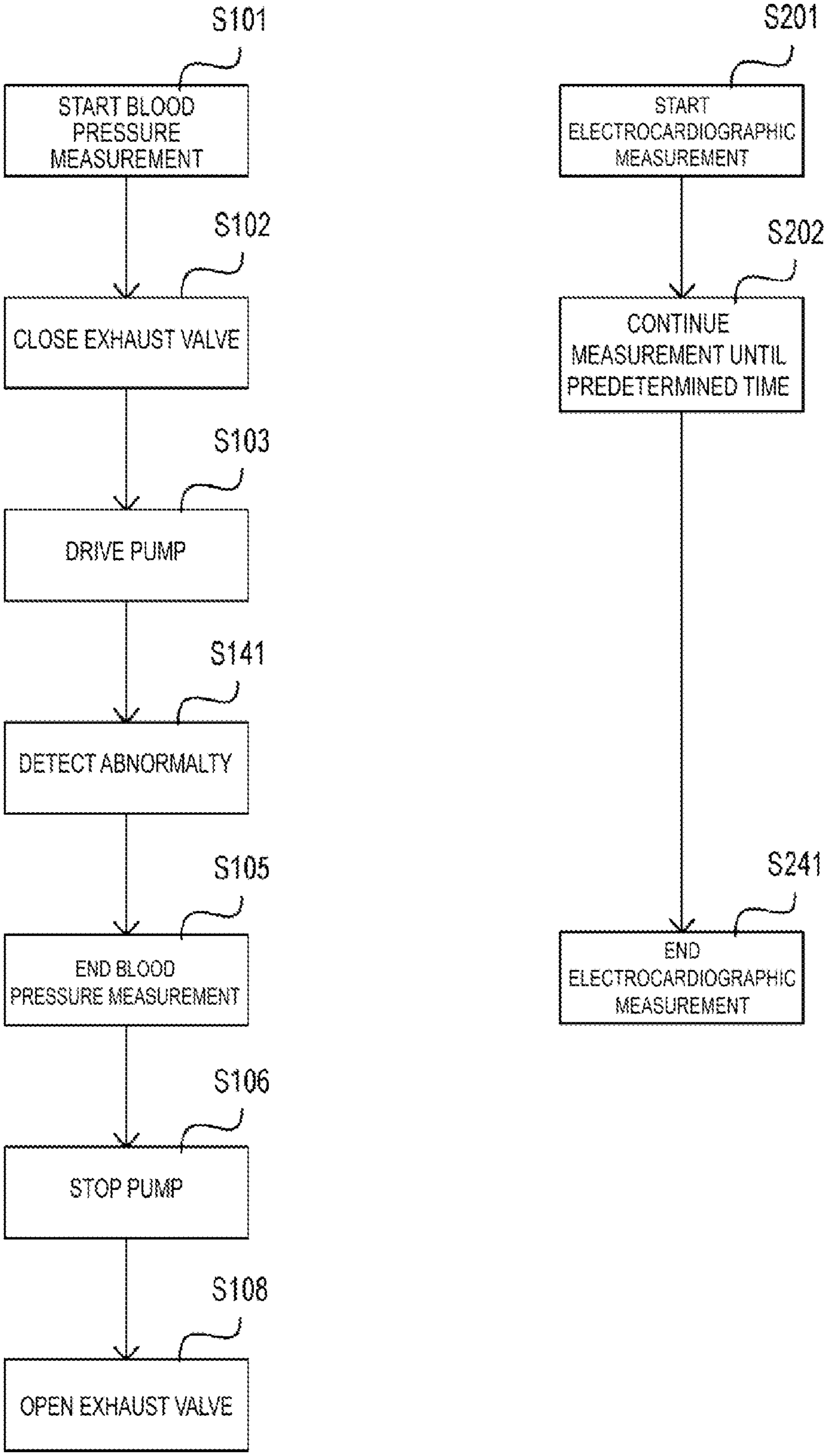

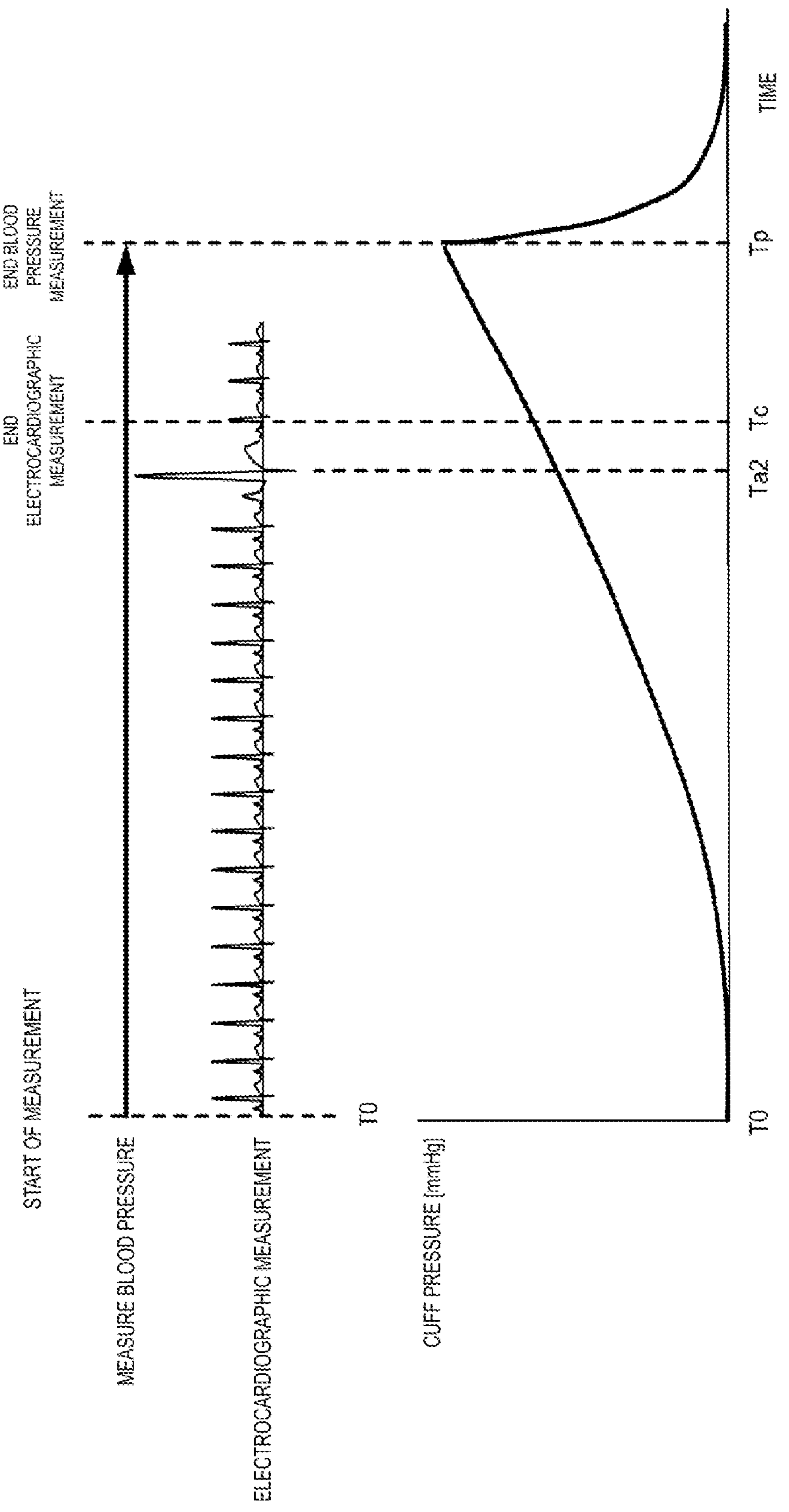
[FIG. 12]

[FIG. 13]
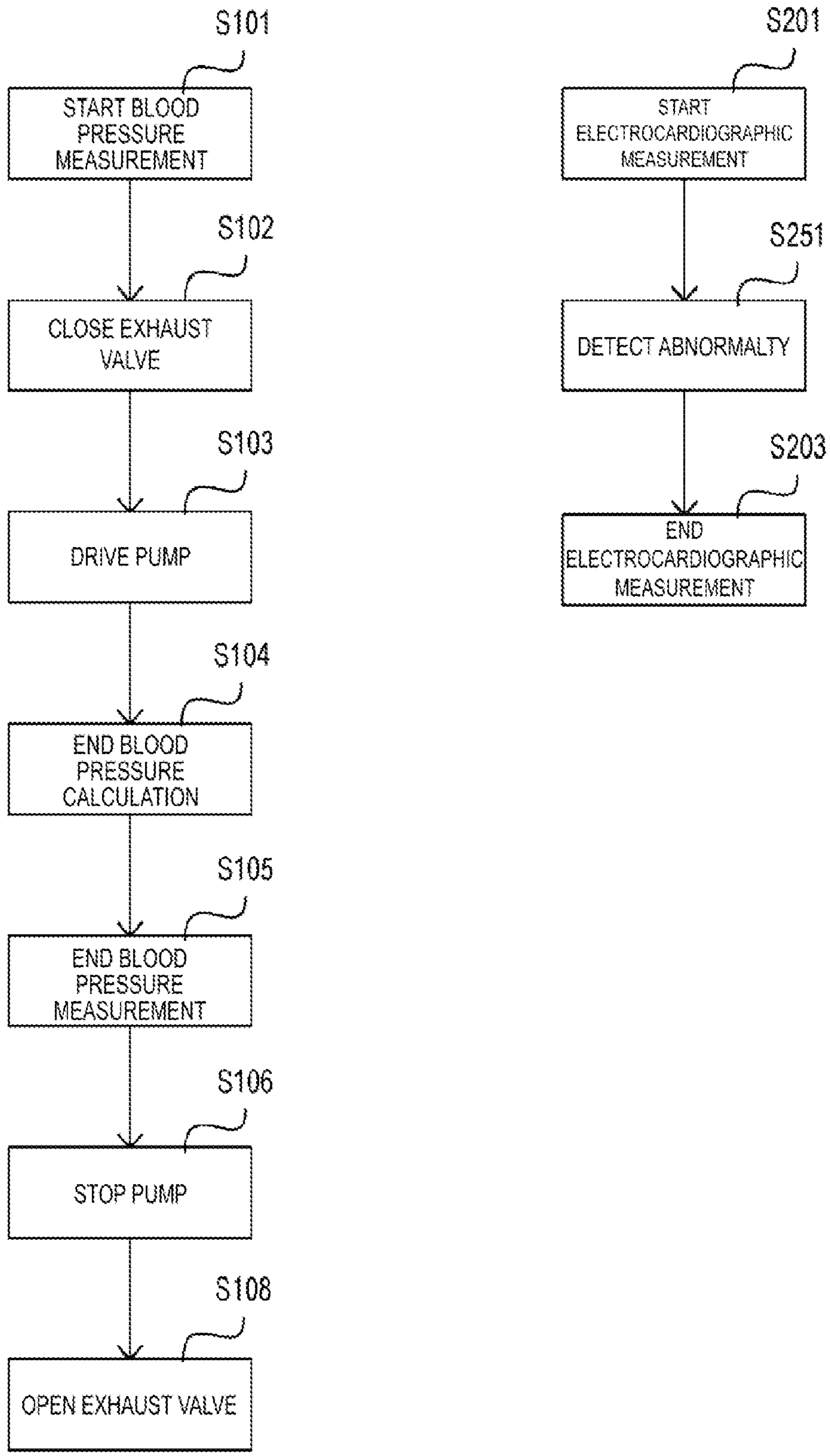

LIVING BODY INFORMATION MEASURING INSTRUMENT AND METHOD FOR CONTROLLING LIVING BODY INFORMATION MEASURING INSTRUMENT

CROSS-REFERENCE TO RELATED APPLICATIONS

This application is the U.S. national stage application filed pursuant to 35 U.S.C. 365(c) and 120 as a continuation of International Patent Application No. PCT/JP2021/020511, filed May 28, 2021, which application is incorporated herein by reference in its entirety.

TECHNICAL FIELD

The present invention relates to a biological information measurement device and a method for controlling the biological information measurement device.

BACKGROUND ART

As a conventional biological information measurement device that simultaneously performs blood pressure measurement and electrocardiographic waveform measurement, a configuration including a housing and a cuff, with an electrode attached to the cuff, has been proposed, as described in Patent Document 1.

CITATION LIST; PATENT LITERATURE

Patent Document 1: JP 2014-36843 A

SUMMARY OF INVENTION

Technical Problem

However, in such a configuration in which a contact state of an electrode is stabilized by inflation of a cuff, there is a problem in that when a state of the cuff rapidly changes due to an end of blood pressure measurement or the like during electrocardiographic waveform measurement, significant noise due to the rapid change in the contact state of the electrode is generated in an electrocardiographic waveform.

In view of the above-described problem, it is an object of the present invention to provide a technique capable of stably measuring an electrocardiographic waveform in a biological information measurement device that simultaneously performs blood pressure measurement and electrocardiographic waveform measurement.

Solution to Problem

In order to solve the above problems, the present invention is a biological information measurement device including a blood pressure measurement unit including a blood pressure measurement control unit configured to control a cuff configured to compress a target measurement site of a subject, a pump configured to supply gas into the cuff, an exhaust valve configured to adjust exhaust of the gas from the cuff, and a pressure detection unit configured to detect a cuff pressure that is a pressure in the cuff, the blood pressure measurement unit being configured to measure a blood pressure of the subject, and an electrocardiographic measurement unit configured to measure an electrocardiographic waveform by processing an electrical signal obtained through a plurality of electrodes that can come into contact with a skin of the subject, in which the blood pressure measurement control unit executes pressurization control of supplying the gas from the pump to the cuff to increase the cuff pressure and pressure reduction control of opening the exhaust valve to rapidly reduce the cuff pressure, and holds the cuff pressure constant or gradually changes the cuff pressure before executing the pressure reduction control when the electrocardiographic measurement unit continues to measure the electrocardiographic waveform at the end of the pressurization control.

In the present invention, in the biological information measurement device including the blood pressure measurement unit and the electrocardiographic measurement unit and the plurality of electrodes for measuring the electrocardiographic waveform include an electrode provided on the target measurement site side of the cuff, when the blood pressure measurement control unit executes the pressurization control of supplying the gas from the pump to the cuff to increase the cuff pressure and the pressure reduction control of opening the exhaust valve to rapidly decrease the cuff pressure, the cuff pressure is held constant or gradually changed before executing the pressure reduction control when the electrocardiographic measurement unit continues to measure the electrocardiographic waveform at the end of the pressurization control. Thus, the cuff pressure does not rapidly change during the measurement of the electrocardiographic waveform, and thus the electrocardiographic waveform can be stably measured.

Further, in the present invention, when the electrocardiographic measurement unit continues to measure the electrocardiographic waveform at the end of the pressurization control, the blood pressure measurement control unit may, before executing the pressure reduction control, control the pump so that the cuff pressure increases more gradually than an increase rate of the cuff pressure at the end of the pressurization control, or may control the exhaust valve so that the cuff pressure decreases more gradually than a decrease rate of the cuff pressure during the pressure reduction control.

According to this, when the electrocardiographic measurement unit continues to measure the electrocardiographic waveform at the end of the pressurization control, the cuff pressure can be gradually changed by controlling the pump so that the cuff pressure increases more gradually than the increase rate of the cuff pressure at the end of the pressurization control before executing the pressure reduction control. Thus, the cuff pressure does not rapidly change during the measurement of the electrocardiographic waveform, and thus the electrocardiographic waveform can be stably measured. Further, when the electrocardiographic measurement unit continues to measure the electrocardiographic waveform at the end of the pressurization control, the cuff pressure can be gradually changed by controlling the exhaust valve so that the cuff pressure decreases more gradually than the decrease rate of the cuff pressure during the pressure reduction control before executing the pressure reduction control. Thus, the cuff pressure does not rapidly change during the measurement of the electrocardiographic waveform, and thus the electrocardiographic waveform can be stably measured.

Further, in the present invention, when the blood pressure measurement control unit detects an abnormality, the blood pressure measurement control unit may stop the pressurization control and execute the pressure reduction control, and the electrocardiographic measurement unit may end the measurement of the electrocardiographic waveform.

According to this, when the blood pressure measurement control unit detects the abnormality, the blood pressure measurement control unit stops the pressurization control and executes the pressure reduction control, and thus when there is the abnormality in the blood pressure measurement, the target measurement site of the subject is not further pressed by the cuff, and a burden on the subject is reduced. On the other hand, the electrocardiographic measurement unit ends the measurement of the electrocardiographic waveform, and thus the measurement of an unstable electrocardiographic waveform including noise generated by the rapid decrease of the cuff pressure is not performed.

Further, in the present invention, when the electrocardiographic measurement unit detects an abnormality before ending the pressurization control, the electrocardiographic measurement unit may end the measurement of the electrocardiographic waveform, and the blood pressure measurement control unit may continue the execution of the pressurization control.

According to this, when the electrocardiographic measurement unit detects the abnormality before ending the pressurization control, the electrocardiographic measurement unit ends the measurement of the electrocardiographic waveform, and thus it is not necessary to continue the measurement of an inaccurate electrocardiographic waveform. On the other hand, even when the measurement of the electrocardiographic waveform is ended, the blood pressure measurement is generally not affected, and thus the execution of the pressurization control is continued for the blood pressure measurement, and the normal blood pressure measurement can be performed.

Further, in the present invention, a display unit configured to display information and a display control unit configured to control the display unit may be included, and the display control unit may display the fact that there is the abnormality in the measurement of the blood pressure on the display unit.

According to this, when the blood pressure measurement control unit detects the abnormality, the pressurization control is stopped, the pressure reduction control is executed, and the measurement of the electrocardiographic waveform is ended, and thus the subject can be notified of the abnormal end of the blood pressure measurement by displaying on the display unit the fact that there is the abnormality in the measurement of the blood pressure. In addition to the fact that there is the abnormality in the blood pressure measurement, the fact that the measurement of the electrocardiographic waveform is ended may be displayed.

Further, in the present invention, a display unit configured to display information and a display control unit configured to control the display unit may be included, and the display control unit may display the fact that there is the abnormality in the measurement of the electrocardiographic waveform on the display unit after the end of the blood pressure measurement.

According to this, when the electrocardiographic measurement unit detects the abnormality, the measurement of the electrocardiographic waveform is ended, but the blood pressure measurement is continued, and thus when the display unit displays the fact that there is the abnormality in the electrocardiographic measurement during the blood pressure measurement, there is a possibility that the subject performs an action affecting the blood pressure measurement such as changing a posture of the subject, and accurate blood pressure measurement is hindered. Thus, by displaying the fact that there is the abnormality in the measurement of the electrocardiographic waveform on the display unit after the end of the blood pressure measurement, the normal measurement of the blood pressure can be performed.

Further, the present invention is a method for controlling a biological information measurement device, the biological information measurement device including a blood pressure measurement unit including a cuff configured to compress a target measurement site of a subject, a pump configured to supply gas into the cuff, and an exhaust valve configured to adjust exhaust of the gas from the cuff, the blood pressure measurement unit being configured to measure a blood pressure of the subject, and an electrocardiographic measurement unit configured to measure an electrocardiographic waveform by processing an electrical signal obtained through a plurality of electrodes that can come into contact with a skin of the subject, the method including a pressurization step of increasing a cuff pressure that is a pressure in the cuff by supplying the gas from the pump to the cuff and a pressure reduction step of rapidly reducing the cuff pressure by opening the exhaust valve, and a step of holding the cuff pressure constant or gradually changing the cuff pressure before executing the pressure reduction control when the measurement of the electrocardiographic waveform continues at the end of the pressurization step.

In the present invention, in the method for controlling the biological information measurement device including the blood pressure measurement unit and the electrocardiographic measurement unit and the plurality of electrodes for measuring the electrocardiographic waveform include an electrode provided on the target measurement site side of the cuff, the method includes a pressurization step of increasing a cuff pressure that is a pressure in the cuff by supplying the gas from the pump to the cuff, and a pressure reduction step of rapidly reducing the cuff pressure by opening the exhaust valve, and a step of holding the cuff pressure constant or gradually changing the cuff pressure before executing the pressure reduction control when the measurement of the electrocardiographic waveform continues at the end of the pressurization step. Thus, the cuff pressure does not rapidly change during the measurement of the electrocardiographic waveform, and thus the electrocardiographic waveform can be stably measured.

Further, in the present invention, when the measurement of the electrocardiographic waveform continues at the end of the pressurization step, before the pressure reduction step, the pump may be controlled so that the cuff pressure increases more gradually than an increase rate of the cuff pressure at the end of the pressurization step, or the exhaust valve may be controlled so that the cuff pressure decreases more gradually than a decrease rate of the cuff pressure in the pressure reduction step.

According to this, when the measurement of the electrocardiographic waveform is continued at the end of the pressurization step, the cuff pressure can be gradually changed by controlling the pump before the pressure reduction step so that the cuff pressure increases more gradually than the increase rate of the cuff pressure at the end of the pressurization step. Thus, the cuff pressure does not rapidly change during the measurement of the electrocardiographic waveform, and thus the electrocardiographic waveform can be stably measured. Further, when the measurement of the electrocardiographic waveform is continued at the end of the pressurization step, the cuff pressure can be gradually changed by controlling the exhaust valve before the pressure reduction step so that the cuff pressure decreases more gradually than the decrease rate of the cuff pressure in the pressure reduction step. Thus, the cuff pressure does not rapidly change during the measurement of the electrocardiographic waveform, and thus the electrocardiographic waveform can be stably measured.

Further, in the present invention, when the blood pressure measurement unit detects the abnormality, the pressurization step may be stopped and the pressure reduction step may be executed, and the measurement of the electrocardiographic waveform may be ended.

According to this, when the blood pressure measurement unit detects the abnormality, the blood pressure measurement unit stops the pressurization step and executes the pressure reduction step, and thus when there is the abnormality in the blood pressure measurement, the target measurement site of the subject is not further pressed by the cuff, and the burden on the subject is reduced. On the other hand, the electrocardiographic measurement unit ends the measurement of the electrocardiographic waveform, and thus the measurement of an unstable electrocardiographic waveform including noise generated by the rapid decrease of the cuff pressure is not performed.

Further, in the present invention, when the electrocardiographic measurement unit detects the abnormality before ending the pressurization step, the measurement of the electrocardiographic waveform may be stopped, and the pressurization step may be continued.

According to this, when the electrocardiographic measurement unit detects the abnormality before ending the pressurization step, the electrocardiographic measurement unit ends the measurement of the electrocardiographic waveform, and thus it is not necessary to continue the measurement of the inaccurate electrocardiographic waveform. On the other hand, even when the measurement of the electrocardiographic waveform is ended, the blood pressure measurement is generally not affected, and thus the pressurization step is continued for the blood pressure measurement, and the normal blood pressure measurement can be performed.

Advantageous Effects of Invention

According to the present invention, a technique capable of stably measuring an electrocardiographic waveform in a biological information measurement device that simultaneously performs blood pressure measurement and electrocardiographic waveform measurement can be provided.

BRIEF DESCRIPTION OF DRAWINGS

Various embodiments are disclosed, by way of example only, with reference to the accompanying schematic drawings in which corresponding reference symbols indicate corresponding parts, in which:

FIG. 1 is a functional block diagram illustrating a biological information measurement device according to Example 1.

FIG. 2 is a graph showing progress of blood pressure measurement and electrocardiographic measurement and a temporal change of a cuff pressure of the biological information measurement device according to a conventional example.

FIG. 3 is a flowchart illustrating a procedure of the blood pressure measurement and the electrocardiographic measurement of the biological information measurement device according to the conventional example.

FIG. 4 is a graph showing progress of blood pressure measurement and electrocardiographic measurement and a temporal change of a cuff pressure of the biological information measurement device according to Example 1.

FIG. 5 is a flowchart illustrating a procedure of the blood pressure measurement and the electrocardiographic measurement of the biological information measurement device according to Example 1.

FIG. 6 is a graph showing progress of blood pressure measurement and electrocardiographic measurement and a temporal change of a cuff pressure of the biological information measurement device according to Example 2.

FIG. 7 is a flowchart illustrating a procedure of the blood pressure measurement and the electrocardiographic measurement of the biological information measurement device according to Example 2.

FIG. 8 is a graph showing progress of blood pressure measurement and electrocardiographic measurement and a temporal change of a cuff pressure of the biological information measurement device according to Example 3.

FIG. 9 is a flowchart illustrating a procedure of the blood pressure measurement and the electrocardiographic measurement of the biological information measurement device according to Example 3.

FIG. 10 is a graph showing progress of blood pressure measurement and electrocardiographic measurement and a temporal change of a cuff pressure of the biological information measurement device according to Example 4.

FIG. 11 is a flowchart illustrating a procedure of the blood pressure measurement and the electrocardiographic measurement of the biological information measurement device according to Example 4.

FIG. 12 is a graph showing progress of blood pressure measurement and electrocardiographic measurement and a temporal change of a cuff pressure of the biological information measurement device according to Example 5.

FIG. 13 is a flowchart illustrating a procedure of the blood pressure measurement and the electrocardiographic measurement of the biological information measurement device according to Example 5.

DESCRIPTION OF EMBODIMENTS

Embodiments of the present invention will be specifically described below with reference to the drawings. It should be noted that the dimension, material, shape, relative arrangement, and the like of the components described in the present examples are not intended to limit the scope of this invention to them alone, unless otherwise stated.

Example 1, Example 1 of the present invention will be described below.

Configuration of Biological Information Measurement Device

FIG. 1 is a block diagram illustrating a schematic configuration of a biological information measurement device 100 according to the present embodiment. The biological information measurement device 100 mainly includes a main body housing 110, a cuff assembly portion 120, and a belt portion 130.

The main body housing 110 includes a display unit 111, a power source unit 112, a blood pressure measurement unit 113, and an electrocardiographic measurement unit 114.

The display unit 111 displays various types of information including guidance to a user when performing blood pressure measurement and measurement of an electrocardiographic waveform (hereinafter also referred to as "electrocardiographic measurement"), and information related to a measurement state and a measurement result.

The power source unit 112 supplies power to the blood pressure measurement unit 113 and the electrocardiographic measurement unit 114, and includes, for example, a rechargeable battery.

The blood pressure measurement unit 113 performs blood pressure measurement together with the cuff assembly portion 120. The blood pressure measurement unit 113 includes a control unit 1131, a calculation unit 1132, a pressure detection unit 1133, a pump 1134, and an exhaust valve 1135. The control unit 1131 has a function of controlling a blood pressure measurement operation performed by the blood pressure measurement unit 113, includes, for example, a CPU and a memory, executes a control program stored in the memory, and controls the pressure detection unit 1133, the pump 1134, the exhaust valve 1135, the display unit 111, and the like, and thus realizing the blood pressure measurement operation. A part or all of the control unit 1131 may be realized by a hardware circuit such as an ASIC or an FPGA. The calculation unit 1132 has a function of executing calculation processing necessary for the blood pressure measurement, includes, for example, a CPU and a memory, and executes a calculation program stored in the memory. The pump 1134 supplies gas (for example, air) into a cuff 1202 to be described later, and the exhaust valve 1135 is a valve that adjusts the exhaust of the gas from the cuff 1202. The blood pressure measurement unit 113 corresponds to the blood pressure measurement unit of the present invention. Here, the blood pressure measurement control unit of the present invention includes the control unit 1131.

The electrocardiographic measurement unit 114 includes a control unit 1141 and a calculation unit 1142. The control unit 1141 has a function of controlling an electrocardiographic measurement operation performed by the electrocardiographic measurement unit 114, includes, for example, a CPU and a memory, executes a control program stored in the memory, and realizes electrocardiographic measurement via a first electrode 1203, a second electrode 1204, and a third electrode 115. The control unit 1141 includes known components such as an amplifier and an AD converter for processing an electrical signal detected by the first electrode 1203, the second electrode 1204, and the third electrode 115. The calculation unit 1142 has a function of executing calculation processing necessary for the electrocardiographic measurement, includes, for example, a CPU and a memory, and executes a calculation program stored in the memory. The electrocardiographic measurement unit 114 corresponds to the electrocardiographic measurement unit of the present invention. The first electrode 1203, the second electrode 1204, and the third electrode 115 correspond to a plurality of electrodes of the present invention that can come into contact with the skin of the subject.

The cuff assembly portion 120 includes a curler 1201, the cuff 1202, the first electrode 1203, and the second electrode 1204. The cuff assembly portion 120 is an assembly including the cuff 1202. The cuff 1202 is a belt-like member and includes a bag-like body therein. The curler 1201 is a plate-like resin member curved in the longitudinal direction so as to surround the target measurement site such as the wrist or the like in the circumferential direction. The cuff 1202 is attached to the inner circumferential side of the curler 1201, and the curler 1201 functions as a base unit that holds the cuff 1202. The first electrode 1203 and the second electrode 1204 are disposed on the inner circumferential side of the cuff 1202. As the target measurement site, an appropriate site such as the wrist or an upper arm can be selected.

The belt portion 130 is a belt-like member, and the curler 1201 is attached to the inner circumferential side of the belt portion 130. The belt portion 130 is wound around the wrist or the like of the subject, adjusted to an appropriate length in accordance with the thickness of the wrist or the like of the subject, and fixed by fixing means such as a buckle or a hook-and-loop fastener.

The third electrode 115 is electrically connected to the control unit 1141 of the electrocardiographic measurement unit 114 together with the first electrode 1203 and the second electrode 1204. The third electrode 115 is disposed at a position allowing contact with a part of the body of the subject so as to be able to detect an electrocardiographic waveform such as V1 induction of the subject together with the first electrode 1203 and the second electrode 1204 that come in contact with the wrist or the like of the subject. For example, when the belt portion 130 is attached to the left wrist of the subject, the third electrode 115 can be provided on a side surface portion of the main body housing 110 with which the subject can come into contact by a finger of the right hand. In this way, the electrocardiographic waveform of I induction can be detected by the first electrode 1203, the second electrode 1204, and the third electrode 115. The position at which the third electrode 115 is provided is not limited thereto.

In the biological information measurement device according to the present example, the blood pressure and the electrocardiographic waveform are measured in parallel. In order to obtain a stable electrocardiographic waveform, it is necessary to continuously measure the electrocardiographic waveform over a period of about 30 seconds. On the other hand, the blood pressure measurement can generally be ended in a period shorter than 30 seconds, although the period varies depending on a physique of the subject, a capacity of the pump, and the like. Thus, when the blood pressure measurement and the electrocardiographic measurement are simultaneously started, the blood pressure measurement may be ended before the electrocardiographic measurement.

FIG. 2 shows the progress from the start of the blood pressure measurement and the electrocardiographic measurement and the temporal change of the cuff pressure. FIG. 3 is a flowchart illustrating a general procedure of the blood pressure measurement and the electrocardiographic measurement. As illustrated in FIG. 3, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, when the electrocardiographic measurement is started, the control unit 1141 continues the electrocardiographic measurement until a predetermined time (step S202). The blood pressure measurement unit 113 measures the blood pressure by, for example, an oscillometric method. That is, the pressure detection unit 1133 detects the cuff pressure and a pulse wave superimposed thereon, and performs predetermined processing on information related to the pulse wave in the calculation unit 1132 to calculate the blood pressure (diastolic blood pressure and systolic blood pressure). When the calculation of the blood pressure is ended (step S104), the blood pressure measurement is ended (step S105). When the blood pressure measurement is ended, the control unit 1131 stops the pump 1134 (step S106) and opens the exhaust valve 1135 (step S108). On the other hand, when the electrocardiographic measurement unit 114 measures the electrocardiographic waveform for a predetermined time, the control unit 1141 ends the electrocardiographic measurement (step S203).

As shown in FIG. 2, the cuff pressure gradually increases from a point in time T0 of starting of the blood pressure measurement and the electrocardiographic measurement. Then, the pump 1134 is stopped from a point in time Tp of when the blood pressure measurement ends, and the exhaust valve 1135 is opened. As a result, the air inside the cuff 1202 is rapidly exhausted, and thus the contact states of the first electrode 1203 and the second electrode 1204 provided on the inner circumferential side of the cuff 1202 are rapidly changed, and noise Ns is generated in the electrocardiographic waveform.

FIG. 4 illustrates the progress from the start of the blood pressure measurement and the electrocardiographic measurement and the temporal change of the cuff pressure in the biological information measurement device 100 according to Example 1. FIG. 5 illustrates a procedure of the blood pressure measurement and the electrocardiographic measurement as a method for controlling the biological information measurement device 100 according to Example 1.

As illustrated in FIG. 5, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, when the electrocardiographic measurement is started, the control unit 1141 continues the electrocardiographic measurement until a predetermined time (step S202). In the blood pressure measurement unit 113, the pressure detection unit 1133 detects the cuff pressure and the pulse wave superimposed thereon by the oscillometric method, and performs predetermined processing on information related to the pulse wave in the calculation unit 1132 to calculate the blood pressure (diastolic blood pressure and systolic blood pressure). When the calculation of the blood pressure is ended (step S104), the blood pressure measurement is ended (step S105). When the blood pressure measurement is ended, the control unit 1131 stops the pump 1134 (step S106). The control unit 1131 stops the pump 1134, but maintains a state in which the exhaust valve 1135 is closed to hold the cuff pressure constant. On the other hand, when the electrocardiographic measurement unit 114 measures the electrocardiographic waveform for a predetermined time, the control unit 1141 ends the electrocardiographic measurement (step S203). The control unit 1131 stops the pump 1134 until the electrocardiographic measurement is ended (determination of No in step S107), and opens the exhaust valve 1135 when the electrocardiographic measurement is ended (determination of Yes in step S107) (step S108). The control unit 1131 of the blood pressure measurement unit 113 may open the exhaust valve 1135 after waiting for the elapse of the electrocardiographic measurement period, or may open the exhaust valve 1135 upon receiving a notification of the end of the electrocardiographic measurement from the control unit 1141 of the electrocardiographic measurement unit 114. Here, the control by the control unit 1131 from closing of the exhaust valve 1135 (step S102) and driving of the pump 1134 (step S103) to stopping of the pump (step S106) corresponds to the pressurization control and the pressurization step of the present invention. The opening of the exhaust valve 1135 by the control unit 1131 (step S108) corresponds to the pressure reduction control and the pressure reduction step of the present invention.

In Example 1, as shown in FIG. 4, the cuff pressure increases from the point in time T0 of starting of the blood pressure measurement to the point in time Tp of ending of the blood pressure measurement, and since the pump 1134 stops at the point in time Tp of ending of the blood pressure measurement to stop the pressurization, and a state where the exhaust valve 1135 is closed is maintained, the cuff pressure is held constant. Then, the exhaust valve 1135 is opened after waiting for a point in time Tc of ending of the electrocardiographic measurement, and thus the cuff pressure rapidly decreases.

As described above, in the biological information measurement device 100 according to Example 1, when the blood pressure measurement is ended and the pressurization of the cuff pressure is ended but the electrocardiographic measurement is continued, the cuff pressure is held constant, and thus the contact states of the first electrode 1203 and the second electrode 1204 are not rapidly changed. Thus, the electrocardiographic measurement unit 114 can perform stable electrocardiographic measurement even after the blood pressure measurement is ended.

Example 2

A biological information measurement device 200 according to Example 2 of the present invention will be described below. Configurations common to those in Example 1 are denoted by the same reference numerals, and detailed description thereof will be omitted. The configuration of the biological information measurement device 200 according to Example 2 is common to the biological information measurement device 100 according to Example 1 illustrated in FIG. 1, and thus description thereof will be omitted.

FIG. 6 illustrates the progress from the start of the blood pressure measurement and the electrocardiographic measurement and the temporal change of the cuff pressure in the biological information measurement device 200 according to Example 2. FIG. 7 illustrates a procedure of the blood pressure measurement and the electrocardiographic measurement as a method for controlling the biological information measurement device 200 according to Example 2.

As illustrated in FIG. 7, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, when the electrocardiographic measurement is started, the control unit 1141 continues the electrocardiographic measurement until a predetermined time (step S202). In the blood pressure measurement unit 113, the pressure detection unit 1133 detects the cuff pressure and the pulse wave superimposed thereon, and performs predetermined processing on information related to the pulse wave in the calculation unit 1132 to calculate the blood pressure (diastolic blood pressure and systolic blood pressure). When the calculation of the blood pressure is ended (step S104), the blood pressure measurement is ended (step S105). When the blood pressure measurement is ended, the control unit 1131 stops the pump 1134 (step S106). The control unit 1131 stops the pump 1134, but controls an opening degree of the exhaust valve 1135 to gradually exhaust the air inside the cuff 1202 (step S121). On the other hand, when the electrocardiographic measurement unit 114 measures the electrocardiographic waveform for a predetermined time, the control unit 1141 ends the electrocardiographic measurement (step S203). The control unit 1131 controls an opening degree of the exhaust valve 1135 until the electrocardiographic measurement is ended (determination of No in step S122), and opens the exhaust valve 1135 when the electrocardiographic measurement is ended (determination of Yes in step S122) (step S108). The control unit 1131 of the blood pressure measurement unit 113 may open the exhaust valve 1135 after waiting for the elapse of the electrocardiographic measurement period, or may open the exhaust valve 1135 upon receiving a notification of the end of the electrocardiographic measurement from the control unit 1141 of the electrocardiographic measurement unit 114. Here, the control by the control unit 1131 from closing of the exhaust valve 1135 (step S102) and driving of the pump 1134 (step S103) to stopping of the pump (step S106) corresponds to the pressurization control and the pressurization step of the present invention. The opening of the exhaust valve by the control unit 1131 (step S108) corresponds to the pressure reduction control and the pressure reduction step of the present invention.

In Example 2, as shown in FIG. 6, the cuff pressure increases from the point in time T0 of starting of the blood pressure measurement to the point in time Tp of ending of the blood pressure measurement, and since the pump 1134 stops at the point in time Tp of ending of the blood pressure measurement to stop the pressurization, and the opening degree of the exhaust valve 1135 is controlled and the air inside the cuff 1202 is gradually exhausted, the cuff pressure also gradually decreases. Then, the exhaust valve 1135 is opened after waiting for the point in time Tc of ending of the electrocardiographic measurement, and thus the cuff pressure rapidly decreases. At this time, a decrease rate of the cuff pressure from the point in time Tp of ending of the blood pressure measurement (that is, the point in time of ending of the pressurization control and the pressurization step) to the point in time Tc of ending of the electrocardiographic measurement is controlled so as to decrease more gradually than a decrease rate of the cuff pressure during the pressure reduction control after the point in time Tc of ending of the electrocardiographic measurement.

As described above, in the biological information measurement device 200 according to Example 2, while the electrocardiographic measurement is continued after the blood pressure measurement is ended, the contact states of the first electrode 1203 and the second electrode 1204 are not rapidly changed by controlling the exhaust valve 1135 to gradually exhaust the air. Thus, the electrocardiographic measurement unit 114 can perform stable electrocardiographic measurement even after the blood pressure measurement is ended.

Example 3

A biological information measurement device 300 according to Example 3 of the present invention will be described below. Configurations common to those in Examples 1 and 2 are denoted by the same reference numerals, and detailed description thereof will be omitted. The configuration of the biological information measurement device 300 according to Example 3 is common to the biological information measurement device 100 according to Example 1 illustrated in FIG. 1, and thus description thereof will be omitted.

FIG. 8 illustrates the progress from the start of the blood pressure measurement and the electrocardiographic measurement and the temporal change of the cuff pressure in the biological information measurement device 300 according to Example 3. FIG. 9 illustrates a procedure of the blood pressure measurement and the electrocardiographic measurement as a method for controlling the biological information measurement device 300 according to Example 3.

As illustrated in FIG. 9, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, when the electrocardiographic measurement is started, the control unit 1141 continues the electrocardiographic measurement until a predetermined time (step S202). In the blood pressure measurement unit 113, the pressure detection unit 1133 detects the cuff pressure and the pulse wave superimposed thereon, and performs predetermined processing on information related to the pulse wave in the calculation unit 1132 to calculate the blood pressure (diastolic blood pressure and systolic blood pressure). When the calculation of the blood pressure is ended (step S104), the blood pressure measurement is ended (step S105). When the blood pressure measurement is ended, the control unit 1131 controls a flow rate of the pump 1134 while keeping the exhaust valve 1135 closed (step S131). The air is continuously fed into the cuff 1202 from the pump 1134, and thus the cuff pressure continues to gradually increase. On the other hand, when the electrocardiographic measurement unit 114 measures the electrocardiographic waveform for a predetermined time, the control unit 1141 ends the electrocardiographic measurement (step S203). The control unit 1131 controls the flow rate of the pump 1134 until the electrocardiographic measurement is ended (determination of No in step S132), stops the pump 1134 (step S106) when the electrocardiographic measurement is ended (determination of Yes in step S132), and opens the exhaust valve 1135 (step S108). The control unit 1131 of the blood pressure measurement unit 113 may stop the pump 1134 after waiting for the elapse of the electrocardiographic measurement period, or may stop the pump 1134 upon receiving a notification of the end of the electrocardiographic measurement from the control unit 1141 of the electrocardiographic measurement unit 114. Here, the control by the control unit 1131 from closing of the exhaust valve 1135 (step S102) and driving of the pump 1134 (step S103) to the end of the blood pressure measurement (step S105) corresponds to the pressurization control and the pressurization step of the present invention. The opening of the exhaust valve by the control unit 1131 (step S108) corresponds to the pressure reduction control and the pressure reduction step of the present invention.

In Example 3, as shown in FIG. 8, the cuff pressure increases from the point in time T0 of starting of the blood pressure measurement to the point in time Tp of ending of the blood pressure measurement, and since the flow rate of the pump 1134 is controlled from the point in time Tp of ending of the blood pressure measurement, the cuff pressure continues to increase more gradually with a smaller slope. Then, the pump 1134 is stopped and the exhaust valve 1135 is opened after waiting for the point in time Tc of ending of the electrocardiographic measurement, and thus the cuff pressure rapidly decreases. At this time, an increase rate of the cuff pressure from the point in time Tp of ending of the blood pressure measurement (that is, the point in time of ending of the pressurization control and the pressurization step) to the point in time Tc of ending of the electrocardiographic measurement is controlled so as to increase more gradually than an increase rate of the cuff pressure at the point in time Tp of ending of the blood pressure measurement, that is, at the end of the pressurization control and the pressurization step.

As described above, in the biological information measurement device 300 according to Example 3, while the electrocardiographic measurement is continued after the blood pressure measurement is ended, the contact states of the first electrode 1203 and the second electrode 1204 are not rapidly changed by controlling the flow rate of the pump 1134 to perform pressurization gradually. Thus, the electrocardiographic measurement unit 114 can perform stable electrocardiographic measurement even after the blood pressure measurement is ended.

Example 4

A biological information measurement device 400 according to Example 4 of the present invention will be described below. Configurations common to those in Example 1 are denoted by the same reference numerals, and detailed description thereof will be omitted. The configuration of the biological information measurement device 400 according to Example 4 is common to the biological information measurement device 100 according to Example 1 illustrated in FIG. 1, and thus description thereof will be omitted.

FIG. 10 illustrates the progress from the start of the blood pressure measurement and the electrocardiographic measurement and the temporal change of the cuff pressure in the biological information measurement device 400 according to Example 4. FIG. 11 illustrates a procedure of the blood pressure measurement and the electrocardiographic measurement as a method for controlling the biological information measurement device 400 according to Example 4.

In Example 4, processing performed when the abnormality is detected during the blood pressure measurement will be described. As illustrated in FIG. 11, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, when the electrocardiographic measurement is started, the control unit 1141 continues the electrocardiographic measurement until a predetermined time (step S202). When the pump 1134 is driven to pressurize the cuff 1202, the control unit 1131 detects the abnormality (step S141). When detecting the abnormality, the control unit 1131 ends the blood pressure measurement (step S105). At the same time that the control unit 1131 ends the blood pressure measurement, the control unit 1141 ends the electrocardiographic measurement (step S241). The control unit 1141 receives a notification of at least one of the abnormality detection and the end of blood pressure measurement from the control unit 1131, and ends the electrocardiographic measurement based on the notification. When the blood pressure measurement is ended, the control unit 1131 stops the pump 1134 (step S106) and opens the exhaust valve 1135 (step S108). At this time, the control unit 1131 notifies the subject of the fact that there is the abnormality by causing the display unit 111 to display a message or an image at an appropriate timing after the time of abnormality detection (step S141). Here, the control by the control unit 1131 from the closing of the exhaust valve 1135 (step S102) and the driving of the pump 1134 (step S103) to the stopping of the pump (step S106) corresponds to the pressurization control and the pressurization step of the present invention, and thus the above-described time of abnormality detection (step S141) corresponds to before the end of the pressurization control and before the end of the pressurization step of the present invention. The opening of the exhaust valve by the control unit 1131 (step S108) corresponds to the pressure reduction control and the pressure reduction step of the present invention. The control unit 1131 corresponds to the display control unit of the present invention.

As shown in FIG. 10, the cuff pressure increases from the point in time T0 of starting of the blood pressure measurement and the electrocardiographic measurement, the pump 1134 is stopped at a point in time Ta1 when the abnormality is detected, and the exhaust valve 1135 is opened. As a result, the air inside the cuff 1202 is rapidly exhausted, and thus the contact states of the first electrode 1203 and the second electrode 1204 provided on the inner circumference of the cuff 1202 are rapidly changed, and stable electrocardiographic measurement cannot be expected. Thus, the electrocardiographic measurement is also ended at the same time as the blood pressure measurement is ended. At the time of blood pressure measurement, the cuff is pressurized and the wrist of the subject is pressed, and the burden on the subject is high, and thus when the abnormality is detected in the blood pressure measurement, it is desirable to give priority to blood pressure measurement abnormality processing. Thus, when the abnormality is detected in the blood pressure measurement, the blood pressure measurement is ended, the pump 1134 is immediately stopped, and the exhaust valve 1135 is opened. Further, such measures make it difficult to perform stable electrocardiographic measurement, and thus the electrocardiographic measurement is also simultaneously ended.

Example 5

A biological information measurement device 500 according to Example 5 of the present invention will be described below. Configurations common to those in Example 1 are denoted by the same reference numerals, and detailed description thereof will be omitted. The configuration of the biological information measurement device 500 according to Example 5 is common to the biological information measurement device 100 according to Example 1 illustrated in FIG. 1, and thus description thereof will be omitted.

FIG. 12 illustrates the progress from the start of the blood pressure measurement and the electrocardiographic measurement and the temporal change of the cuff pressure in the biological information measurement device 500 according to Example 5. FIG. 13 illustrates a procedure of the blood pressure measurement and the electrocardiographic measurement as a method for controlling the biological information measurement device 500 according to Example 5.

In Example 5, processing performed when the abnormality is detected during the electrocardiographic measurement will be described. As illustrated in FIG. 13, simultaneously with the start of the blood pressure measurement (step S101), the electrocardiographic measurement is started (step S201). When the blood pressure measurement is started, the control unit 1131 closes the exhaust valve 1135 (step S102), drives the pump 1134 (step S103), and feeds air into the cuff 1202 to pressurize the cuff 1202. On the other hand, during the electrocardiographic measurement, the control unit 1141 detects the abnormality (step S251). When detecting the abnormality, the control unit 1141 ends the electrocardiographic measurement without waiting for the elapse of a predetermined time (step S203). At this stage, the control unit 1141 does not notify the subject of the fact that there is the abnormality. The blood pressure measurement unit 113 continues the blood pressure measurement operation regardless of the end of the electrocardiographic measurement by the electrocardiographic measurement unit 114. That is, in the blood pressure measurement unit 113, the pressure detection unit 1133 detects the cuff pressure and the pulse wave superimposed thereon, and performs predetermined processing on information related to the pulse wave in the calculation unit 1132 to calculate the blood pressure (diastolic blood pressure and systolic blood pressure). When the calculation of the blood pressure is ended (step S104), the blood pressure measurement is ended (step S105). When the blood pressure measurement is ended, the control unit 1131 stops the pump 1134 (step S106) and opens the exhaust valve 1135 (step S108). The control unit 1141 notifies the subject that the electrocardiographic measurement is abnormal by causing the display unit 111 to display a message or an image at an appropriate timing after the end of the blood pressure measurement (step S105). Here, the control by the control unit 1131 from closing of the exhaust valve 1135 (step S102) and driving of the pump 1134 (step S103) to stopping of the pump (step S106) corresponds to the pressurization control and the pressurization step of the present invention. The opening of the exhaust valve by the control unit 1131 (step S108) corresponds to the pressure reduction control and the pressure reduction step of the present invention. The control unit 1141 corresponds to the display control unit of the present invention.

As shown in FIG. 12, the blood pressure measurement and the electrocardiographic measurement proceed from the point in time T0 of starting of the blood pressure measurement and the electrocardiographic measurement, and the cuff pressure increases accordingly. The control unit 1141 detects the abnormality at a point in time Ta2 in the middle of the parallel progress of the blood pressure measurement and the electrocardiographic measurement, and ends the electrocardiographic measurement. The blood pressure measurement is continued after the point in time Tc of ending of the electrocardiographic measurement, and the cuff pressure continues to increase. Thereafter, at the point in time Tp of when the blood pressure measurement ends, the pump 1134 is stopped and the exhaust valve 1135 is opened, and thus the cuff pressure rapidly decreases.

As described above, the burden on the subject in the electrocardiographic measurement is lower than in the blood pressure measurement, and thus priority is given to the blood pressure measurement. In addition, when the abnormality in the electrocardiographic measurement is notified to the subject during the blood pressure measurement, there is a possibility that the blood pressure measurement is affected by an action of the subject such as releasing the third electrode 115 or touching it again. Thus, the abnormality in the electrocardiographic measurement is not notified until the blood pressure measurement is ended, and the abnormality in the electrocardiographic measurement is notified after the blood pressure measurement is ended.

REFERENCE NUMERALS LIST

100, 200, 300, 400, 500 Biological information measurement device
113 Blood pressure measurement unit
114 Electrocardiographic measurement unit
115 Third electrode
1131 Control unit
1133 Pressure detection unit
1134 Pump
1135 Exhaust valve
1141 Control unit
1202 Cuff
1203 First electrode
1204 Second electrode

What is claimed is:

1. A biological information measurement device comprising:

a blood pressure measurement unit including a blood pressure measurement control unit configured to control a cuff configured to compress a target measurement site of a subject, a pump configured to supply gas into the cuff, an exhaust valve configured to adjust exhaust of the gas from the cuff, and a pressure detection unit configured to detect a cuff pressure that is a pressure in the cuff, the blood pressure measurement unit being configured to measure a blood pressure of the subject; and an electrocardiographic measurement unit configured to measure an electrocardiographic waveform by processing an electrical signal obtained through a plurality of electrodes that can come into contact with a skin of the subject, wherein the electrocardiographic measurement unit continuously measures the electrocardiographic waveform for a predetermined electrocardiographic measurement period from start of blood pressure measurement; and the blood pressure measurement control unit executes pressurization control of supplying the gas from the pump to the cuff to increase the cuff pressure from the start of blood pressure measurement and pressure reduction control of opening the exhaust valve to rapidly reduce the cuff pressure, and holds the cuff pressure constant or gradually changes the cuff pressure before executing the pressure reduction control when it is determined whether the electrocardiographic measurement unit has ended measurement of the electrocardiographic waveform and it is determined that the electrocardiographic measurement unit continues to measure the electrocardiographic form at the end of the pressurization control.

2. The biological information measurement device according to claim 1, wherein when it is determined that the electrocardiographic measurement unit continues to measure the electrocardiographic waveform at the end of the pressurization control, the blood pressure measurement control unit, before executing the pressure reduction control, controls the pump so that the cuff pressure increases more gradually than an increase rate of the cuff pressure at the end of the pressurization control, or controls the exhaust valve so that the cuff pressure decreases more gradually than a decrease rate of the cuff pressure during the pressure reduction control.

3. The biological information measurement device according to claim 2, wherein when the blood pressure measurement control unit detects an abnormality, the blood pressure measurement control unit stops the pressurization control and executes the pressure reduction control, and the electrocardiographic measurement unit ends the measurement of the electrocardiographic waveform.

4. The biological information measurement device according to claim 2, wherein when the electrocardiographic measurement unit detects an abnormality before ending the pressurization control, the electrocardiographic measurement unit ends the measurement of the electrocardiographic waveform, and the blood pressure measurement control unit continues the execution of the pressurization control.

5. The biological information measurement device according to claim 1, wherein when the blood pressure measurement control unit detects an abnormality, the blood pressure measurement control unit stops the pressurization control and executes the pressure reduction control, and the electrocardiographic measurement unit ends the measurement of the electrocardiographic waveform.

6. The biological information measurement device according to claim 5, further comprising:

a display unit configured to display information; and a display control unit configured to control the display unit, wherein the display control unit displays the fact that there is the abnormality in the measurement of the blood pressure on the display unit.

7. The biological information measurement device according to claim 5, wherein when the electrocardiographic measurement unit detects an abnormality before ending the pressurization control, the electrocardiographic measurement unit ends the measurement of the electrocardiographic waveform, and the blood pressure measurement control unit continues the execution of the pressurization control.

8. The biological information measurement device according to claim 1, wherein when the electrocardiographic measurement unit detects an abnormality before ending the pressurization control, the electrocardiographic measurement unit ends the measurement of the electrocardiographic waveform, and the blood pressure measurement control unit continues the execution of the pressurization control.

9. The biological information measurement device according to claim 8, further comprising:

a display unit configured to display information; and a display control unit configured to control the display unit, wherein the display control unit displays the fact that there is the abnormality in the measurement of the electrocardiographic waveform on the display unit after the end of the blood pressure measurement.

10. A method for controlling a biological information measurement device, the biological information measurement device comprising:

a blood pressure measurement unit including a cuff configured to compress a target measurement site of a subject, a pump configured to supply gas into the cuff, and an exhaust valve configured to adjust exhaust of the gas from the cuff, the blood pressure measurement unit being configured to measure a blood pressure of the subject; and an electrocardiographic measurement unit configured to measure an electrocardiographic waveform by processing an electrical signal obtained through a plurality of electrodes that can come into contact with a skin of the subject, the method comprising:

continuously measuring the electrocardiographic waveform for a predetermined electrocardiographic measurement period from start of blood pressure measurement, performing pressurization of increasing a cuff pressure that is a pressure in the cuff by supplying the gas from the pump to the cuff from the start of blood pressure measurement, performing pressure reduction of rapidly reducing the cuff pressure by opening the exhaust valve, performing determination of whether measurement of the electrocardiographic waveform has been ended at the end of the pressurization, and holding the cuff pressure constant or gradually changing the cuff pressure before executing the pressure reduction control when it is determined that the measurement of the electrocardiographic waveform continues at the end of the pressurization.

11. The method for controlling a biological information measurement device according to claim 10, wherein when it is determined that the measurement of the electrocardiographic waveform continues at the end of the pressurization, before performing pressure reduction, the pump is controlled so that the cuff pressure increases more gradually than an increase rate of the cuff pressure at the end of the pressurization, or the exhaust valve is controlled so that the cuff pressure decreases more gradually than a decrease rate of the cuff pressure in the pressure reduction.

12. The method for controlling a biological information measurement device according to claim 11, wherein when the blood pressure measurement unit detects an abnormality, the pressurization is stopped and the pressure reduction is executed, and the measurement of the electrocardiographic waveform is ended.

13. The method for controlling a biological information measurement device according to claim 11, wherein when the electrocardiographic measurement unit detects an abnormality before ending the pressurization, the measurement of the electrocardiographic waveform is stopped, and the pressurization is continued.

14. The method for controlling a biological information measurement device according to claim 10, wherein when the blood pressure measurement unit detects an abnormality, the pressurization is stopped and the pressure reduction is executed, and the measurement of the electrocardiographic waveform is ended.

15. The method for controlling a biological information measurement device according to claim 14, wherein when the electrocardiographic measurement unit detects an abnormality before ending the pressurization, the measurement of the electrocardiographic waveform is stopped, and the pressurization is continued.

16. The method for controlling a biological information measurement device according to claim 10, wherein when the electrocardiographic measurement unit detects an abnormality before ending the pressurization, the measurement of the electrocardiographic waveform is stopped, and the pressurization is continued.

* * * * *